United States Patent [19]

Burton

[11] 4,421,740

[45] Dec. 20, 1983

[54] HAIR CONDITIONING COMPOSITION AND PROCESS FOR PRODUCING THE SAME

[75] Inventor: Colin K. Burton, Racine, Wis.

[73] Assignee: S. C. Johnson & Son, Inc., Racine, Wis.

[21] Appl. No.: 3,678

[22] Filed: Jan. 15, 1979

Related U.S. Application Data

[63] Continuation of Ser. No. 860,019, Dec. 12, 1977, abandoned, and Ser. No. 704,000, Jul. 9, 1976, abandoned.

[51] Int. Cl.[3] ........................ A61K 7/06; A61K 47/00

[52] U.S. Cl. ...................................... 424/70; 424/361; 424/362

[58] Field of Search .......................................... 424/70

[56] References Cited

U.S. PATENT DOCUMENTS 3,423,504 1/1969 Birkelo et al. ........................ 424/70
3,577,528 5/1971 McDonough et al. ............... 424/70
3,822,312 7/1974 Sato et al. ......................... 424/70 X

FOREIGN PATENT DOCUMENTS 1439321 4/1966 France ................................. 424/70
1251648 10/1971 United Kingdom .................. 424/70

OTHER PUBLICATIONS

Jungerman et al., Soap and Chemical Specialties, pp. 59–62, Sep. 1964.

Poucher, vol. I, Perfumes, Cosmetics and Soaps, pp. 199 and 247, Chapman and Hall, London; John Wiley & Sons, New York, (1974).

Kirk–Othmer, *Encyclopedia of Chemical Technology*, vol. 10, p. 777, (Second Edition, 1966).

*Primary Examiner*—Dale R. Ore

[57] ABSTRACT

A hair conditioning composition consisting essentially of from about 0.5–2% by weight of a quaternary conditioning compound, from about 0.5–2% by weight of cetyl alcohol, up to about 10.0% by weight of a protective colloid, and from about 99.0–86.0% by weight water; the quaternary conditioning compound and the cetyl alcohol being present in a ratio of from 1.5:1 to 0.42:1, said composition having a viscosity of less than 10,000 centipoise. The above composition is prepared by mixing the water, cetyl alcohol, and quaternary compound at temperatures above the melting points thereof, followed by cooling the same and homogenizing the cooled composition at a pressure of from 500–8,000 psi, this homogenized composition is then mixed with a dispersion of the thickener in water to form the final hair-conditioning composition. A process for conditioning the hair utilizing the composition which comprises cleaning the hair in a conventional manner, applying a composition consisting essentially of from about 0.5–2% by weight of a quaternary conditioning compound, from about 0.5–2% by weight cetyl alcohol, up to about 10.0% by weight of a protective colloid, and from about 99.0–86.0% by weight water to the hair.

3 Claims, 1 Drawing Figure

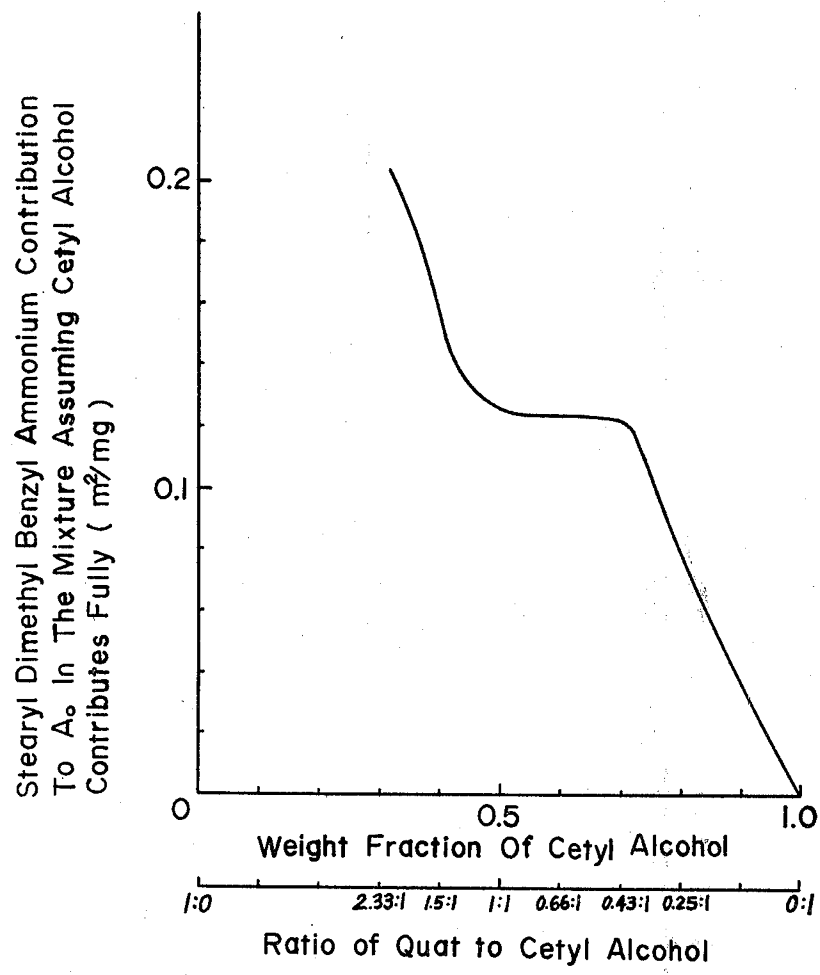
Stearyl Dimethyl Benzyl Ammonium Chloride–Cetyl Alcohol Interaction As A Function Of Concentration
Stearyl Dimethyl Benzyl Ammonium Contribution To A₀ In The Mixture Assuming Cetyl Alcohol Contributes Fully ( m²/mg )
0.2
0.1
0
0.5
1.0
Weight Fraction Of Cetyl Alcohol
1:0
2.33:1
1.5:1
1:1
0.66:1
0.43:1
0.25:1
0:1
Ratio of Quat to Cetyl Alcohol

HAIR CONDITIONING COMPOSITION AND PROCESS FOR PRODUCING THE SAME

This is a continuation of application Ser. No. 704,000, filed July 9, 1976, and Ser. No. 860,019, filed Dec. 12, 1977, both now abandoned.

BACKGROUND OF THE INVENTION

This invention relates to a hair conditioning composition and process for making and using the same. More particularly, this invention relates to a hair conditioning composition, a creme rinse composition, a process for producing a hair conditioning or creme rinse composition which includes homogenizing the composition, and a process for treating the hair.

Although hair conditioners and creme rinses utilize similar ingredients at different concentrations, their uses are substantially different. A hair conditioner is generally utilized as a periodic treatment to restore the condition to hair which has been damaged due to regular use or misuse of hair waving compositions or hair colorant compositions. A creme rinse, however, is generally utilized as an after-shampoo treatment which improves the manageability and combability of the hair. Creme rinses have become particularly attractive to individuals having long hair which subsequent to shampooing becomes difficult to control and comb.

Both hair conditioners and creme rinses generally utilize cationic compounds which are substantive to the hair. These compositions also may include small percentages of waxy materials such as higher alcohols which also appear to effect the condition of the hair. These higher alcohols, although they were recognized as improving conditioning, have had a detrimental effect on the stability of prior art creme rinse products.

Generally prior art creme rinse formulations use about 2.5% to 7% quaternary compound such as stearyl dimethyl benzyl ammonium chloride and may include up to 1% by weight of a oil-soluble waxy material, such as a higher alcohol such as isostearyl alcohol, cetyl alcohol, stearyl alcohol, liquid hexadecanol, or octaphenoxy ethanol, waxy esters such as glycerol mono-, di- and tri-stearate, ethylene glycol mono- and distearate, propylene glycol stearates, sorbitan stearates, etc. These materials are substantially water insoluble and are not selfdispersing, and for this reason only small quantities are used. Water-dispersible or water-soluble materials are often incorporated in prior art compositions in relatively large amounts in attempts to solublize water-insoluble materials or stabilize the formulation. These materials include various water-soluble or dispersible surfactants or salts. Other conventional creme rinse formulations are disclosed on pages 1102–1105 of THE CHEMISTRY AND MANUFACTURE OF COSMETICS, Vol. 4, 2nd edition, by Maison G. deNavarre.

Prior art hair conditioning compounds, as exemplified by pages 1097–1101 of the above book, also include quaternary compounds mixed with higher alcohols. In particular, a formulation described on page 1100 described Adogen 432 CG, a quaternary ammonium compound, mixed with cetyl alcohol, sodium chloride, and water. This composition contains a relatively high percentage of cetyl alcohol and would appear to show that the same is desirable in providing some conditioning properties to the hair.

Prior art compounds used higher levels of quaternary to provide improved performance, as has been noted previously only relative small percentages of cetyl alcohol could be incorporated into the composition without impairing the stability of the compound. Further, prior art compositions generally have what can be best described as a stringy or lumpy appearance or consistency. This is due in part to the natural agglomerative effects of the quaternary compounds themselves. The prior art compositions commonly have particle sizes in the range of 40 to 60 microns or higher.

SUMMARY AND BRIEF DESCRIPTION OF THE INVENTION

It has been, therefore, most surprisingly found that a highly acceptable stable creme rinse formulation and hair conditioning composition can be prepared using a lower level of active ingredients than heretofore thought possible by preparing a composition of from 0.5–2% by weight quaternary conditioning compound, 0.5–2% by weight cetyl alcohol, up to about 10.0% by weight of a protective colloid, and the balance containing water to 100%, this composition having a viscosity of less than 10,000 centipoise when used as a conditioning treatment, and less than 4,000 centipoise when used as a creme rinse.

It is most surprising that the composition of the present invention is quite stable and is readily dispersible in water and provides outstanding performance and properties even at dilute concentrations which were not recognized previously.

The process of preparing the above composition comprises mixing the quaternary compound and water and heating the same, followed by melting the cetyl alcohol and blending these two materials together and cooling the same. This cool mixture is then homogenized at a pressure of from 500–8,000 psi, followed by blending with a dispersion of the thickener in water.

It is, therefore, the primary object of the present invention to provide a readily dispersible and highly acceptable creme rinse formulation.

It is a further object of the present invention to provide a composition utilizing a relatively high ratio of cetyl alcohol to quaternary ammonium compound in a creme rinse composition.

It is a still further object of the present invention to provide excellent performance characteristics of a creme rinse composition, while at the same time having a relatively low level of active ingredients, thereby maintaining a substantail cost savings.

It is a further object of the present invention to provide a process for preparing a highly effective and useful creme rinse and hair conditioning formulation having a relatively stable viscosity profile over extended storage.

It is a still further object of the present invention to provide a process for preparing a readily dispersible creme rinse composition.

It is a still further object of the present invention to provide a composition which has a smooth and creamy appearance after extended storage and does not substantially agglomerate into larger particles.

It is a still further object of the present invention to provide a process for treating the hair utilizing the compositions of the present invention.

Still further objects and advantages of the compositions and processes of the present invention will become more apparent from the following more detailed description thereof and the attached drawing which is a schematic plot of the quaternary contribution to monolayer area versus concentration described in Example 8.

DETAILED DESCRIPTION OF THE INVENTION

The present invention is directed to a hair conditioning composition consisting essentially of from about 0.5–2% by weight of a quaternary conditioning compound, from about 0.5–2% by weight of cetyl alcohol, up to about 10.0% by weight of a protective colloid, and from about 99.0–86.0% by weight water; the quaternary conditioning compound and cetyl alcohol being present in a ratio of from 1.5:1 to 0.42:1, said composition having a viscosity of less than 10,000 centipoise.

The creme rinse composition of the present invention consists essentially of from about 0.5–1.5% by weight of a quaternary conditioning compound, from about 0.5–1.5% by weight of cetyl alcohol, up to about 5.0% by weight of a protective colloid, and from about 99.0–92% by weight water, the quaternary conditioning compound and cetyl alcohol being present in a ratio of from 1.5:1 to 0.66:1, said composition having a viscosity of less than 4,000 centipoise.

The process of the present invention comprises preparing a hair conditioning composition consisting essentially of from about 0.5–2% by weight of a quaternary conditioning compound, from about 0.5–2% by weight cetyl alcohol, up to about 10.0% by weight of a protective colloid, and from about 99.0–86.0% by weight water, the quaternary conditioning compound and cetyl alcohol being present in a ratio of from 1.5:1 to 0.42:1 comprising (1) combining the quaternary conditioning compound, a portion of the water, and the cetyl alcohol at a temperature above 50° C. to form an intermediate, (2) cooling the intermediate to a temperature within the range of from 80°–120° F., (3) homogenizing the intermediate at a pressure of from 500–8,000 psi, (4) dispersing the protective colloid in water, and (5) blending the intermediate and dispersed protective colloid.

The process of conditioning hair of the present invention comprises (1) cleaning the hair and (2) applying from 1 to 5 grams of a composition consisting essentially of from about 0.5–2% by weight of a quaternary conditioning compound, from about 0.5–2% by weight cetyl alcohol, up to about 10.0% by weight of a protective colloid, and from about 99.0–86.0% by weight water, the quaternary conditioning compound and cetyl alcohol being present in a ratio of from 1.5:1 to 0.42:1.

The quaternary conditioning compounds suitable for use in the compositions and processes of the present invention include stearyl dimethyl benzyl ammonium chloride, dihydrogenated tallow dimethyl ammonium chloride, mixed higher alkyl C12–C18 trimethyl ammonium chloride, cetyl dimethyl amine oxide, stearyl dimethyl amine oxide, and mixtures thereof. The preferred quaternary conditioning compound is stearyl dimethyl benzyl ammonium chloride. The quaternary conditioning compound is present in the composition of the present invention in an amount ranging from about 0.5–2% by weight when the composition is designed for use as a hair conditioner and from about 0.5–1.5% by weight when the composition is designed for use as a creme rinse. The preferred composition includes from about 0.75–1.25% by weight quaternary conditioning compound.

The second ingredient used in the composition of the present invention is cetyl alcohol. The cetyl alcohol aids in conditioning the hair. However, unless the composition is homogenized, the cetyl alcohol causes the composition to become unstable. The viscosity of unhomogenized samples rises quite quickly, forming an unusable composition. The cetyl alcohol is present in an amount from about 0.5–2% by weight when the composition is to be used as a conditioner and from about 0.5–1.5% by weight when this composition is to be used as a creme rinse. More particularly, the cetyl alcohol is present in an amount of from about 0.75–1.25% by weight.

The relative ratio of quaternary conditioning compound to cetyl alcohol is from 1.5:1 to 0.42:1 and for a creme rinse preferably from about 1.5:1 to 0.66:1. It is within the above ranges that the conditioning properties of the composition of the present invention and the remarkable stability of this composition is most evident. At ratios above or below the above ratio, the compositions become unstable in that the composition separates unduly on standing or that the composition becomes so thick upon standing as to become unpourable. Furthermore, it is the extremely small particle size dispersion of the creme rinse composition which aids in the desirable performance properties thereof. It is most difficult to maintain this small particle size at ratios outside the above-noted ratios. In this regard, when a quaternary compound such as stearyl dimethyl benzyl ammonium chloride is processed utilizing the process of the present invention without incorporating any cetyl alcohol in the composition, the viscosity is initially low, however, the particles tend to agglomerate and the composition becomes less easily dispersible and in turn as an effective conditioning compound. Also, when cetyl alcohol is added without homogenization, the viscosity of the resultant compositions rises dramatically. Further, even when homogenized, compositions outside the above range exhibit higher viscosities and become more unstable.

When the term viscosity is used in this specification and in the attached claims, it refers to Brookfield Viscosity measured using Brookfield LV Viscometer with either #2 or #3 spindles and from 6 to 60 rpm.

Also, as an aid to stabilize the viscosity of this composition and to impart asthetic qualities, a small amount of a protective colloid may be utilized in an amount of up to about 10% and preferably from 0.1–10% and most preferably 0.1–5%. Suitable protective colloids include various cellulosic derivatives such as methyl cellulose, hydroxyethyl cellulose, ethyl cellulose, quar gums, and various other nonionic or cationic protective colloids, etc., which are known to be cosmetically acceptable. Examples of these materials include thickeners and other compositions sold under the trade names such as Natrosol. Other similar protective colloids can be utilized in the compositions of the present invention as the exact composition of the protective colloid is unimportant so long as the same is cosmetically acceptable and chemically compatible.

The bulk of the composition of the present invention comprises water, i.e., in the range of from 99.0–86.0% by weight. Although tap water can sometimes be used if the same contains a relatively low level of ions, it is preferred to use deionized water.

Also, other conventional additives can be incorporated into the composition of the present invention such as various dyes and perfumes which are cosmetically acceptable. These materials are added in the composition in relatively small amounts and do not affect the overall performance and/or stability thereof. However, salts as are commonly found in prior art compositions should not be incorporated into the compositions as they tend to make the compositions more unstable.

The compositions of the present invention are prepared by means of the process of the present invention which process includes the steps of mixing the quaternary compound and the cetyl alcohol under conditions of agitation and heat prior to homogenizing the same. This mixed composition is then cooled to a temperature in the range of from 80°-120° F., preferably from 100°-110° F. This cooled mixture is then homogenized at 500-8,000 psi. Subsequent to the homogenization step, it is preferred to force cool, i.e., cool rapidly, the intermediate to a temperature in the range of 80°-90° F. This aids in maintaining the desirable small particle size. At this time, a dispersion of the protective colloid is added as well as any perfumes and dyes which may be required. The protective colloid should be well dispersed in water before it is added to the intermediate. Depending on the particular material used, it may be necessary to heat the water-protective colloid mixture to temperatures of up to 200° F. If heat is necessary to completely disperse the protective colloid, this material should be cooled before the blending step. The process of the present invention has the effect of providing a composition with relatively small particle size. Relatively small particle size is known to produce quaternary compositions which are considerably more active than similar compositions with a larger particle size. In this regard, it is found that the compositions of the present invention effectively form a very thin film having a degree of integrity approaching mono-layer type properties and have the combined properties of the quaternary compound and the cetyl alcohol.

The primary purpose or object of the process of the present invention is to provide a final product with as small a particle size as possible and to insure that the particle size remains small over standing. As has been disclosed in U.S. Pat. No. 3,954,634 which discloses the concept of homogenizing quaternary compounds to improve the particle size of the resultant dispersion and stability thereof, a smaller particle size enables the quaternary compound to act more efficiently.

The compositions of the present invention are ready-to-use hair conditioners or creme rinses which are applied directly to the hair of the user subsequent to shampooing. These compositions are easily and readily dispersible across the hair fibers and forms substantially thin films on the hair fibers to replace the oils which are stripped from the hair during shampooing. Also, the compositions can be readily dispersed in small quantities of water, i.e., from 10-200 ml. of water per 2.5 grams of product.

The composition of the present invention will now be illustrated by way of the following examples which are for the purpose of illustration only and are in no way to be considered as limiting.

EXAMPLE 1

A creme rinse composition having the following composition was prepared:

| | |
|---|---|
| Stearyl dimethyl benzyl ammonium chloride (25% solids) | 3.6 |
| Cetyl alcohol | 1.1 |
| Hydroxyethyl cellulose | 0.75 |
| Perfume | 0.25 |
| Water Q.S. | to 100% |

A portion of the water is mixed with the stearyl dimethyl benzyl ammonium chloride and the mixture is heated to 180° F. The cetyl alcohol is heated to above its melt point, i.e., 150° F., and the melted cetyl alcohol is added to the water-quaternary mixture. This mixture is cooled to between 85° and 100° F. and homogenized at a pressure of 5000 psi. The remaining water is mixed with the hydroxyethyl cellulose and heated to 120° F. with agitation. This dispersion is cooled to 75° F., and the hydroxyethyl cellulose dispersion is blended with the cetyl alcohol-quaternary mixture.

The above composition was tested against a leading commercially available creme rinse and was found to provide excellent conditioning and a cleaner less oily feeling than the leading creme rinse.

EXAMPLE 2

A number of compositions were prepared without the thickener to observe the stability of the composition and the viscosity with and without homogenization.

TABLE I

| Run | Homogenized | % Cetyl Alc. | % Ammonyx[1] | Ratio Cetyl Alc./ Ammonyx | Viscosity Cps 1 day | 1 week | 2 weeks | 3 weeks |
|---|---|---|---|---|---|---|---|---|
| A | Yes | 0.6 | 0.9 | 3:2 | 6 | 7 | 7 | 6* |
| B | Yes | 0.75 | 0.75 | 1:1 | 5 | 9 | 6 | 9 |
| C | Yes | 0.9 | 0.6 | 2:3 | 40 | 200 | 340 | 710 |
| D | Yes | 0.8 | 1.2 | 3:2 | 7 | 8 | 6 | 8* |
| E | Yes | 1.0 | 1.0 | 1:1 | 7 | 9 | 10 | 16 |
| F | Yes | 0.8 | 0.8 | 2:3 | 60 | 560 | 890 | 1290 |
| G | No | 0.6 | 0.9 | 3:2 | 7 | 10 | 10 | 11* |
| H | No | 0.75 | 0.75 | 1:1 | 9 | 15 | 16 | 25 |
| I | No | 0.9 | 0.6 | 2:3 | 1200 | 1740 | 1890 | 1960 |
| K | No | 1.0 | 1.0 | 1:1 | 13 | 43 | 94 | 134 |
| L | No | 1.2 | 0.8 | 2:3 | 2130 | 2610 | 2740 | 2620 |
| M | Yes | 1.0 | 1.5 | 3:2 | 7 | 9 | 9 | 10 |
| N | Yes | 1.25 | 1.25 | 1:1 | 8 | 13 | 25 | 53 |
| O | Yes | 1.5 | 1.0 | 2:3 | 100 | 1080 | 2120 | 2114 |
| P | No | 1.0 | 1.5 | 3:2 | 11 | 27 | 37 | 49 |
| Q | No | 1.25 | 1.25 | 1:1 | 20 | 132 | 232 | 299 |
| R | No | 1.5 | 1.0 | 2:3 | 2790 | 3160 | 3000 | 2940 |
| S | Yes | 1.0 | 0.5 | 2:1 | 2460 | 2610 | 2426 | 2326 |
| T | Yes | 1.34 | 0.66 | 2:1 | 3540 | 3330 | 3140 | 2800 |
| U | Yes | 1.675 | 0.825 | 2:1 | 4640 | 3940 | 3640 | 3360 |
| V | No | 1.0 | 0.5 | 2:1 | 920 | 1640 | 2446 | 2030 |
| W | No | 1.34 | 0.66 | 2:1 | 2210 | 2780 | 2820 | 2910 |

TABLE I-continued

| Run | Homogenized | % Cetyl Alc. | % Ammonyx[1] | Ratio Cetyl Alc./ Ammonyx | Viscosity Cps 1 day | 1 week | 2 weeks | 3 weeks |
|---|---|---|---|---|---|---|---|---|
| X | No | 1.675 | 0.825 | 2:1 | 3560 | 3806 | 3400 | 3410 |

*Sample slightly separated
[1]Ammonyx 4 calculated as 100% solids, stearyl dimethyl benzyl ammonium chloride As is apparent from the above table, the viscosity increases as concentration increases or cetyl alcohol increases. Also, the homogenized samples generally have a lower viscosity than non-homogenized samples. On performance, the homogenized samples performed better than the non-homogenized samples.

EXAMPLE 3

The combing ease of a number of samples having different ratios of quaternary to cetyl alcohol by measuring the work required to pass a comb through a hair swatch. The hair was first washed with a commercially available shampoo.

| Run | Ratio of Cetyl Alc:Quat | Value |
|---|---|---|
| A | 0.25:1 | 100 |
| B | 1:1 | 84 |
| C | 2.3:1 | 64 |
| D | 1.5:1 | 80 |
| E | 1.22:1 | 82 |

The lower the value, the easier the combing. As is apparent, Run C (2.3:1) was the easiest. However, at this ratio, the product was extremely viscous even after homogenization. This indicates that higher levels of cetyl alcohol produce more conditioning.

EXAMPLE 4 AND COMPARATIVE EXAMPLE 1

Two formulations having an identical composition were prepared:

| | |
|---|---|
| Ammonyx 4 (25% solids) (stearyl dimethyl benzyl ammonium chloride) | 7.2 |
| Cetyl alcohol | 2.2 |
| Perfume | 0.5 |
| Water Q.S. | to 100% |

The only difference in the compositions is that Example 4 was homogenized at 5,000 psi and had a viscosity of 15 cps, while Comparative Example 1 was not homogenized and had a viscosity of 6,660 cps.

These compositions were applied to 33 models using a half-head technique by professional operators. The models perceived significantly more conditioning in the Example 4 sample at the 95%+ confidence level. Although other preferences were not statistically confident at 95%, the Example 4 composition was generally preferred in almost all attributes of a creme rinse by both models and operators.

EXAMPLE 5 and COMPARATIVE EXAMPLE 2

The following composition was prepared using the procedure of Example 1:

| | |
|---|---|
| Ammonyx 4 (25% solids) | 3.0 |
| Cetyl alcohol | 0.75 |
| Perfume | 0.3 |
| Hydroxyethyl cellulose | 0.75 |
| Water | 95.20 |
| | 100.00 |

The composition was applied at various dilution levels, i.e., 1.0, 2.5, and 4.0 grams in 200 ml. water and compared to Tame, a commercially available creme rinse, at 2.5 grams in 200 ml. water. Tame has an approximate composition by analysis of 2.6% dimethyl stearyl benzyl ammonium chloride and 1.8% polyethoxylated long-chain fatty alcohol.

The models statistically preferred the composition of Example 5 at all three use levels in areas of residue on comb, lubricity, clean feel, wet preference, and dry preference. Although the 1.0 gram dilution did not provide as good combing as the 2.5 and 4.0 samples, it did condition at a level equal to or better than Tame at much lower solids level.

EXAMPLE 6

The composition of Example 1 was compared to a commercially available creme rinse having a composition by analysis of 1.9% dimethyl stearyl benzyl ammonium chloride, 0.5% polyethoxylated ester, 6.8% a mix of fatty esters, fatty alcohols and hydrocarbon oil, and 0.9% protein derivative at equal use levels on 34 models. The composition of Example 1 was found significantly more conditioned, both wet and dry, and had less residue on the comb, left the hair feeling cleaner and with less flyaway.

EXAMPLE 7

A composition was prepared using the procedure of Example 1 having the formula:

| | |
|---|---|
| Ammonyx 4 (25% solids) | 3.33 |
| Cetyl alcohol | 1.02 |
| Perfume | 0.24 |
| Hydroxyethyl cellulose | 0.75 |
| Water Q.S. | to 100% |

The ratio of quat to cetyl alcohol is 45/55 at 1.8% solids. This formula was significantly preferred by 31 models and the professional operators over Tame, a commercially available creme rinse, in areas of oily feel, clean feel, easier rinsing, less residue, less coated, overall preferences, and body and manageability.

EXAMPLE 8

In order to determine if there is any molecular interaction between the cetyl alcohol and quaternary compounds at the ratios of the compositions of the present invention, a mono-layer study on a 5% NaCl aqueous solution using the Wilhelmy method was performed on a series of mixtures of cetyl alcohol (Aldol 52) and stearyl dimethyl benzyl ammonium chloride (Ammonyx 4). The mixtures were prepared in a hexane-ethanol solvent spreading medium. The surface tension, $\gamma$, of the 5% NaCl solution is measured as the spread mono-layer is slowly compressed. The film pressure, $\pi$, is equal to the difference between $\gamma_o$, the surface tension of the clean substrate, and $\gamma$ the measured surface tension of the film-covered substrate. The limiting area $A_o$ is the film area at the film collapse point and represents the area of closest packing.

The schematic graph in the attached drawing is developed using the following analysis technique. Y, the assumed contribution of the quaternary, equals the observed $A_o$ minus contribution of cetyl alcohol, assuming the cetyl alcohol acts as if nothing else was present in the system. The observed $A_o$ was taken for a number of mixtures and Y values were calculated and plotted versus weight fraction. The observed $A_o$ was measured using the apparatus described in ACS Symposium Series #8, Adsorption at Interfaces, Monolayer Studies V, pages 157-169 (1975) and J. Colloidal & Interface Science, V28, page 481 (1968).

As shown by the schematic plot within the ratios of the compositions of the present invention, there is a shoulder indicating some interaction between the cetyl alcohol and quaternary compound.

What is claimed is:

1. A process for preparing a stable hair conditioning composition consisting essentially of from about 0.5 to 2% by weight of a conditioning compound selected from the group consisting of stearyl dimethyl benzyl ammonium chloride, dihydrogenated tallow dimethyl ammonium chloride, mixed C12-C18 alkyl trimethyl ammonium chloride, cetyl dimethyl amine oxide, stearyl dimethyl amine oxide, and mixtures thereof; from about 0.5 to 2% by weight cetyl alcohol; from about 0.1 to about 10% by weight of a protective colloid selected from the group consisting of methyl cellulose, ethyl cellulose, hydroxyethyl cellulose, guar gum, and mixtures thereof; and 86-99% by weight water, the conditioning compound and cetyl alcohol being present in a ratio of from about 1.5:1 to 0.42:1 which comprises (a) combining the conditioning compound, water, and cetyl alcohol at a temperature above 50° C. to form an intermediate;

(b) cooling the intermediate to a temperature within the range of from 80°-120° F.;

(c) homogenizing the intermediate at a pressure of from 500-8,000 psi;

(d) dispensing the protective colloid in water; and (e) blending the intermediate and dispersed protective colloid.

2. The process of claim 1 which includes the step (c') force cooling the intermediate to a temperature of 80°-90° F.

3. The process of claim 1 wherein the intermediate is cooled to a temperature of about 100°-110° F.

* * * * *